United States Patent
Kamiyama

[11] Patent Number: 5,993,391
[45] Date of Patent: Nov. 30, 1999

[54] ULTRASOUND DIAGNOSTIC APPARATUS

[75] Inventor: Naohisa Kamiyama, Otawara, Japan

[73] Assignee: Kabushiki Kaisha Toshiba, Kawasaki, Japan

[21] Appl. No.: 09/159,507

[22] Filed: Sep. 24, 1998

[30] Foreign Application Priority Data

Sep. 25, 1997 [JP] Japan .................................. 9-259891

[51] Int. Cl.⁶ .................................................. A61B 8/00
[52] U.S. Cl. .......................................... 600/443; 128/916
[58] Field of Search .................................. 600/407, 437, 600/443–447, 916

[56] References Cited

U.S. PATENT DOCUMENTS

| | | | |
|---|---|---|---|
| 4,821,728 | 4/1989 | Ledley | 600/447 |
| 5,488,952 | 2/1996 | Schoolman | 600/443 |
| 5,503,152 | 4/1996 | Oakley et al. | 128/916 X |
| 5,694,937 | 12/1997 | Kamiyama . | |
| 5,776,067 | 7/1998 | Kamada et al. | 128/916 X |

FOREIGN PATENT DOCUMENTS

10-90409 4/1998 Japan .

*Primary Examiner*—Francis J. Jaworski
*Attorney, Agent, or Firm*—Oblon, Spivak, McClelland, Maier & Neustadt, P.C.

[57] ABSTRACT

In an ultrasound diagnostic apparatus, ultrasound transmission/reception means transmits and receives ultrasound to and from a subject to obtain an echo signal and an ultrasonic image of a desired tomographic plane of the subject is produced on the basis of the echo signal. The ultrasound diagnostic apparatus comprises image collecting means for collecting ultrasonic images in the direction perpendicular to the tomographic plane, image synthesizing means for synthesizing a stereoscopic right-eye image and a stereoscopic left-eye image from the ultrasonic images, and display means for displaying the right-eye image and the left-eye image separately. Using a relatively small number of images, a simple ultrasonic three-dimensional image with a depth effect is displayed at high speed.

12 Claims, 10 Drawing Sheets

FIG. 10   MOVING SCREEN

LEFT EYE  RIGHT EYE

FIG. 15A  FIG. 15B

LEFT EYE  RIGHT EYE

ULTRASOUND DIAGNOSTIC APPARATUS

BACKGROUND OF THE INVENTION

This invention relates to an ultrasound diagnostic apparatus which generates an ultrasonic image on the basis of phase information and amplitude information contained in the reception signal obtained by scanning a subject by ultrasound, and more particularly to an ultrasound diagnostic apparatus which generates a stereoscopic image from ultrasonic images at high speed and displays the image.

Ultrasound has been applied to various medical instruments. A typical application of ultrasound to medical instruments is an ultrasound diagnostic apparatus for creating a tomographic image of soft part tissue of an organism using ultrasonic pulse reflection techniques. The ultrasound diagnostic apparatus displays a tomographic image of tissue without stress. As compared with the X-ray diagnostic apparatus, X-ray computed tomography apparatus (CT), a magnetic resonance imaging apparatus (MRI), or a nuclear medicine diagnostic apparatus, the ultrasound diagnostic apparatus has the advantages of enabling real-time display, being compact and inexpensive, being sufficiently safe without exposure to X rays, and enabling the imaging of bloodstream by the Doppler ultrasonography.

Because of those advantages, the ultrasound diagnostic apparatus has been widely used in diagnosing internal organs, such as a heart, the abdomen, the mammary gland, or the urinary organs, in internal medicine or in observing a fetus in obstetrics and gynecology.

Specifically, with the ultrasound diagnostic apparatus, simply applying an ultrasonic probe to the surface of a body enables the pulsation of a heart or the movement of a fetus to be displayed in real time. Because the apparatus is very safe, examination can be carried out repeatedly. Moreover, it is easy to move the apparatus to the bedside and carry out examination.

Furthermore, the ultrasound diagnostic apparatus is also capable of displaying the speed distribution of the bloodstream moving toward (or away from) the vibrators in the Doppler ultrasonography or the distribution of power values of the blood echo signal in the power Doppler method. The power Doppler method enables the perfusion of the vascular system to be sensed with higher sensitivity and is finding its way into the diagnosis of an abnormal bloodstream at the peripheral nerve level of a kidney or cancer of the liver.

Like in the fields of CT and MRI, in the field of ultrasonic diagnosis, there has been an increasing demand for three-dimensional images. For example, in the B mode imaging or color Doppler imaging, three-dimensional stereoscopic images have been displayed for the purpose of making a differential diagnosis or functional diagnosis of the shape of an internal organ or the passage of a blood vessel. Since a three-dimensional stereoscopic image has not only information on a two-dimensional image (or a tomographic image) but also information on the direction of its depth, it is expected that the shape of a tissue or the passage of a blood vessel will be known clearly.

Constructing an image having three-dimensional information requires an enormous amount of calculations, which leads to the problem of taking as long a time as several tens of seconds to several minutes to reconstruct and display a single image.

In the case of CT and MRI, because the nature of their diagnosis, spending a substantially long time in constructing a three-dimensional image may often be a negligible problem. In the case of ultrasonic diagnosis, since observation is made in real time, three-dimensional representation is hardly used in normal diagnosis. When a three-dimensional image is constructed in ultrasonic diagnosis, the image has to be reconstructed for observation after the data has been taken in (e.g., after examination), as with CT and MRI.

Although an image containing three-dimensional information enables an image viewed from any viewpoint to be reconstructed, observation from more than one viewpoint takes that much more time. It will be all right if a three-dimensional image (a still image) is observed from more than one viewpoint. In the case of images obtained one after another in real time as ultrasound diagnostic images, it is not always useful to reconstruct those images and see them from another viewpoint. Conversely, this action may make the procedure more complicated and troublesome.

Moreover, accurate three-dimensional information may not be necessary. For example, only an image with a depth effect may be needed to get more accurate information on the shape of a tissue or the passage of a blood vessel.

BRIEF SUMMARY OF THE INVENTION

It is, accordingly, an object of the present invention to overcome the disadvantages in the prior art by providing an ultrasound diagnostic apparatus capable of displaying ultrasound diagnostic images with a three-dimensional effect at high speed.

The foregoing object is accomplished by providing an ultrasound diagnostic apparatus which causes ultrasound transmission/reception means to transmit and receive ultrasound to and from a subject to obtain an echo signal and produces an ultrasonic image of a desired tomographic plane of the subject on the basis of the echo signal, the ultrasound diagnostic apparatus comprising image collecting means for collecting ultrasonic images in the direction perpendicular to the tomographic plane, image synthesizing means for synthesizing a stereoscopic right-eye image and a stereoscopic left-eye image from the ultrasonic images, and display means for displaying the right-eye image and the left-eye image separately.

With this configuration, an ultrasound diagnostic image with a three-dimensional effect of a specific tomographic plane of the subject can be displayed at high speed even in the absence of precise three-dimensional information.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The file of this patent contains at least one color photograph executed in color. Copies of this patent with color photographs will be provided by the Patent and Trademark Office upon request and payment of the necessary fee.

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Hereinafter, referring to the accompanying drawings, embodiments of the present invention will be explained.

Before explanation of embodiments (a first to a fourth embodiment), the principle of the depth sampling method and the principle of stereoscopic vision will be explained.

Figures 9, 10:
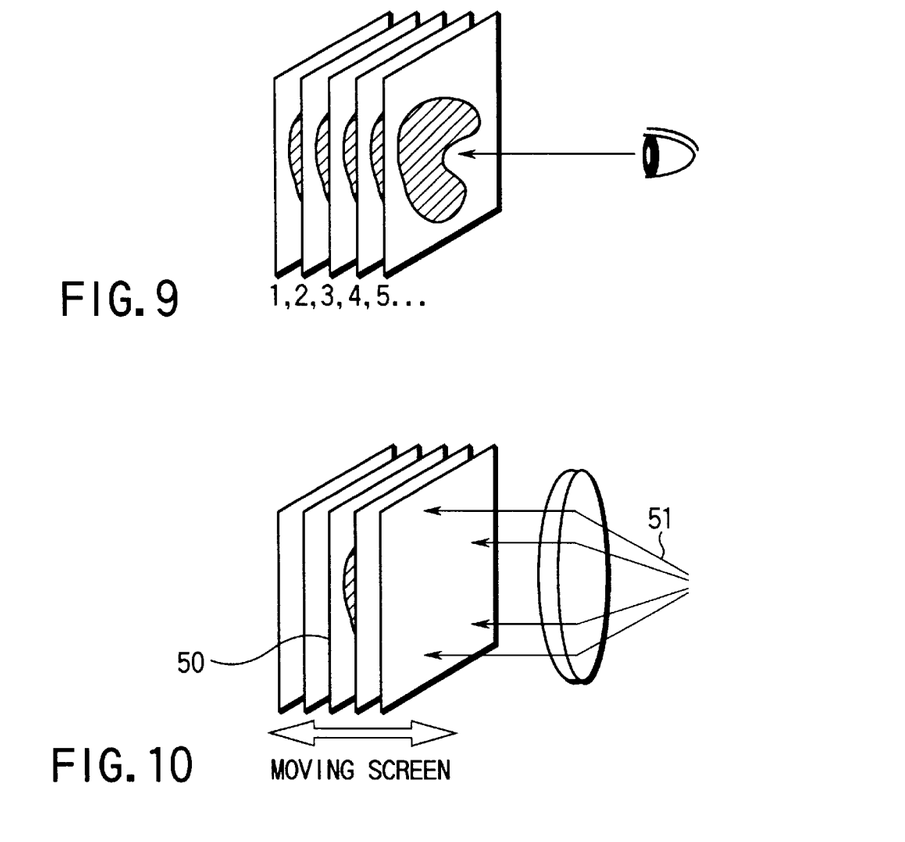
FIG. 9 is a conceptual diagram of a depth tomographic image.
FIG. 10 is a conceptual diagram of a moving screen system.

With not only the ultrasound diagnostic apparatus but also CT and MRI, when more than one two-dimensional tomographic image is viewed in the direction perpendicular to their plane, each cross section can be considered to have a different depth and consequently can be said to have three-dimensional information (refer to FIG. 9). There have been several methods of displaying a three-dimensional image constructed from such tomographic images (referred to as depth sampling tomographic images). Examples of them will be explained below.

One example is a method known as a moving screen method (reference: Hiroaki Yamada, et al., "A moving-screen three-dimensional display", 3D IMAGE, 6-6, pp. 36–41, 1992) as shown in FIG. 10. In the method, laser light 51 is caused to scan a moving (vibrating) screen 50 in such a manner that tomographic image are projected on the screen 50 one after another. Another known example of the method of vibrating the display surface is the variable focal mirror method in which images are reflected by another vibrating mirror to form a stereoscopic image.

Figure 11:
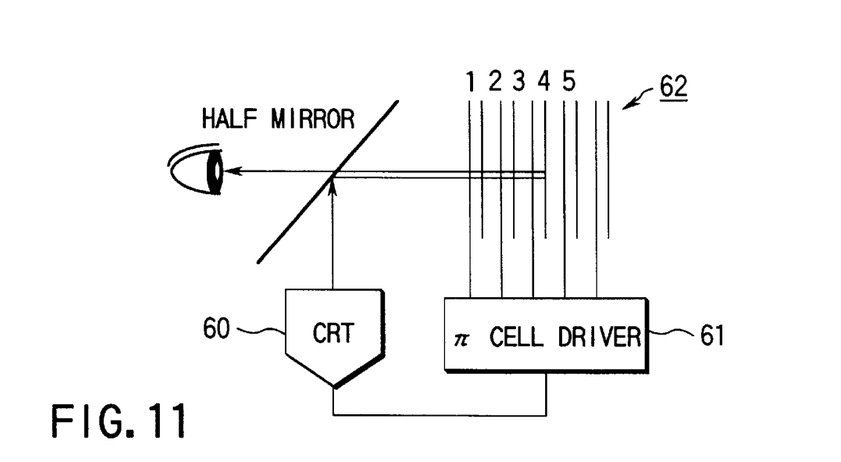
FIG. 11 is a conceptual diagram of a three-dimensional display of the stacked display surface type.

Another example is a method using a display in which display surfaces are stacked (reference: T. S. Bugak, "SID Digest," 1985). It is a method in which display light from a CRT 60 is reflected by liquid-crystal cells 62 corresponding to the depth. In the method, a π-cell driver 61 selectively drives the liquid-crystal cells 62. Therefore, the method has the advantage of requiring no mechanically moving section but has a disadvantage in that images get darker in proportion to the number of liquid-crystal cells the light passes through.

Figure 12:
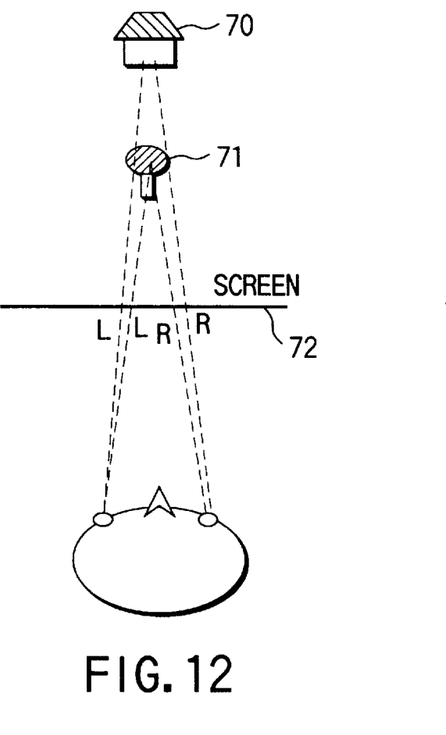
FIG. 12 is an explanatory diagram for binocular parallax.
Figure 13:
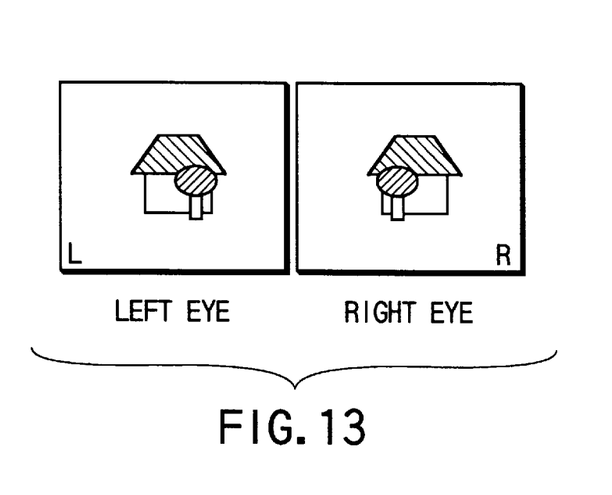
FIG. 13 shows a display example of an image projected to the right and left eyes with binocular parallax.

The principle of stereoscopic vision and a method of realizing it will be explained. Stereoscopic images used in stereoscopic photographs or stereoscopic television are based on the difference between images reflected in the right and left eyes, what is called "binocular parallax." This makes it possible to display an image with a depth effect on a single screen (or two screens because the image reflected in the right eye differs from that in the left eye). For example, consider a case where there is a house 70 in the distance and a tree 71 at close range as shown in FIG. 12. When a screen 72 is placed in a suitable position, it is found that there is a difference between the images projected on the screen 72 as shown in FIG. 13. In FIG. 13, when space separation is effected in such a manner that the left image is visualized only by the left eye and the right image is visualized only by the right eye, the tree is positioned in the front and the house is located at the back.

Figure 14:
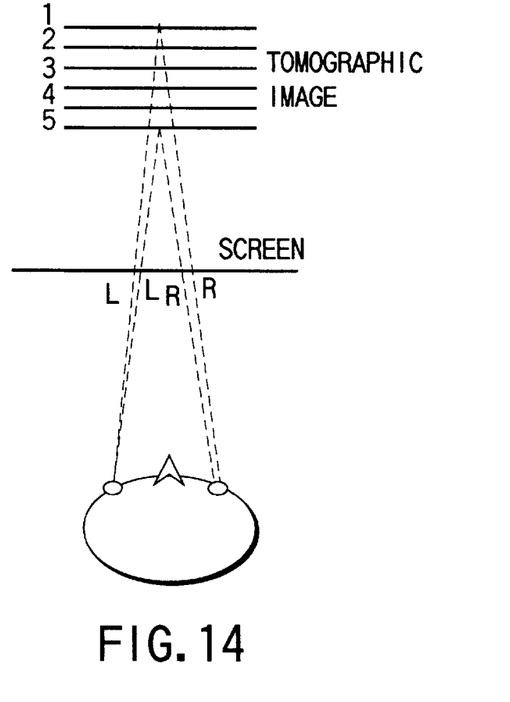
FIG. 14 shows the relationship between the depth tomographic image and the binocular parallax.

The objects (house and tree) shown in FIGS. 12 and 13 are two-dimensional images. When an actual three-dimensional object is viewed, strictly speaking, the shape will vary as much as one viewpoint is away from the other viewpoint by the distance between the right and left eyes. When the aforementioned depth sampling tomographic images are arranged as shown in FIG. 14 and then are projected on the screen 72 as in FIG. 12, this will produce a stereoscopic image as a result of stereoscopic vision. Specifically, the images are synthesized in such a manner that a closer one of the tomographic images for the left eye is shifted more to the right, where as a closer one of the tomographic images for the right eye is shifted more to the left. When images are observed by what is called the crossing method, the images should be shifted in the opposite direction.

There arise two problems. (1) One problem is that it is not necessarily true that the angle at which the right eye sees a thing differs from that at which the left eye sees the thing. If the angles (angles of convergence) need not be so accurate, this problem can be neglected. (2) The other problem is that when most of the images are tomographic images with three-dimensional depth information, it is difficult to project them on a single screen. In the case of dotted objects to be displayed as shown in FIG. 12, it is easy to project them on a single screen.

If more and more tomographic images are used, it will be more difficult to project them on a single screen. Hereinafter, an example of a method of synthesizing images that solves problem (2) will be explained.

(A) Method of using transmission images

Figure 15A:
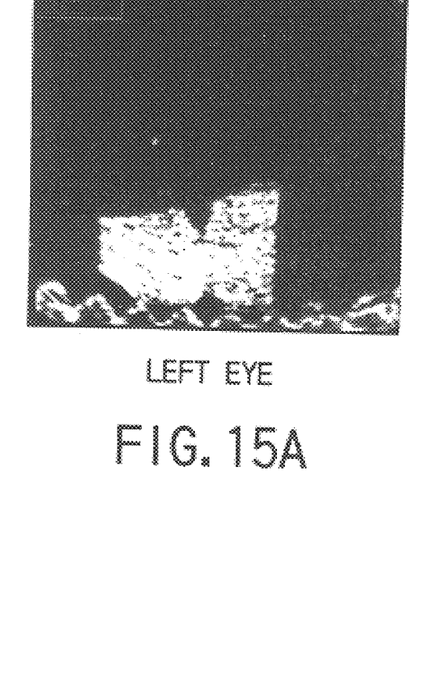
FIG. 15A is a color photograph showing a display example of an image for the left eye by a transmission image technique.
Figure 15B:
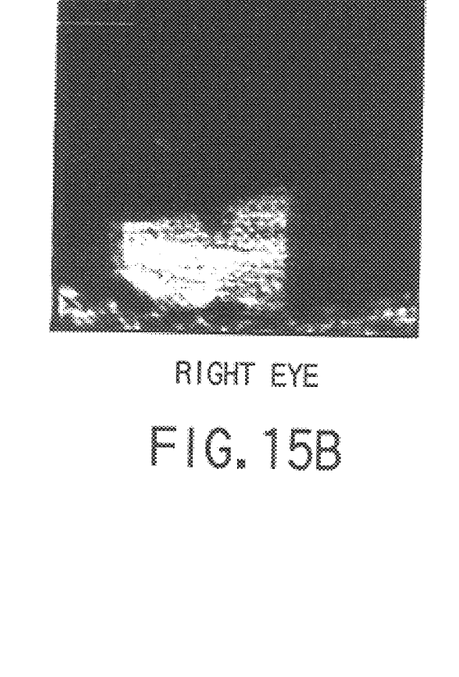
FIG. 15B is a color photograph showing a display example of an image for the right eye by the transmission image technique.

FIGS. 15A and 15B show an example of creating a stereoscopic image from a front transmission image and a back transmission image, which serve as depth sampling tomographic images. FIG. 15A shows a stereoscopic left-eye image and FIG. 15B shows a stereoscopic right-eye image. Each of these left-eye and right-eye images is created, for example, as follows.

A stereoscopic left-eye image is created by halving the intensity of each of the two transmission images and making an additive synthesis of these.

A stereoscopic right-eye image is created by halving the intensity of each of the two transmission images, shifting the front transmission image about eight pixels to the left of the screen, and making an additive synthesis of these.

What is important here is the way of relatively shifting the left-eye and right-eye transmission images. As long as the same effect is produced, the way of shifting the images may be changed arbitrarily. For example, when a transmission image shifted four pixels to the left of the screen is considered to be the original image, if the front transmission image is shifted four pixels to the right of the screen and the front transmission image is shifted four pixels to the left of the screen, a stereoscopic image as described above will be obtained.

As a result, translucent tomographic images are observed in such a manner that they are laid one on top of another, giving a depth effect. When about two or four transmission images are laid one on top of another, ultrasound B mode images are considered to be suitable for stereoscopic images. As more tomographic images are used, the intensity of each image becomes lower. Therefore, it is expected that a good image cannot be obtained (or that an image with a lower transmittance will be obtained).

(B) Method of using MIP

Figure 16A:
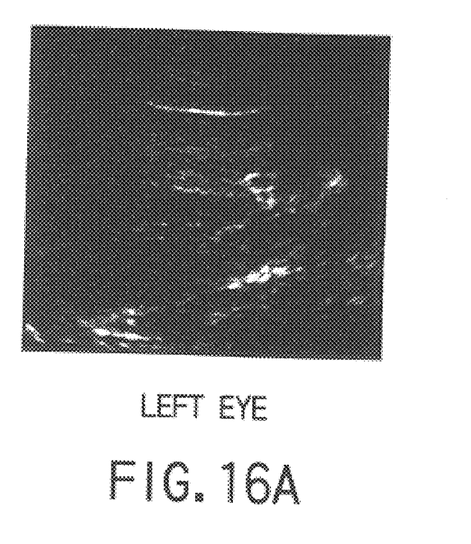
FIG. 16A is a color photograph showing a display example of an image for the left eye by an MIP technique.
Figure 16B:
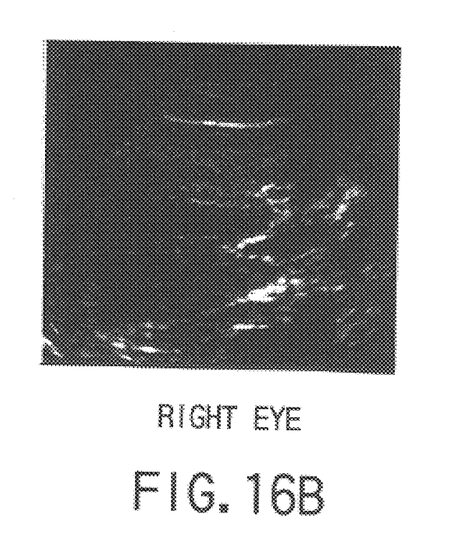
FIG. 16B is a color photograph showing a display example of an image for the right eye by the MIP technique.

FIGS. 16A and 16B show a case where the maximum intensity projection method (MIP) is applied. They shows an example of creating a stereoscopic image from four depth sampling tomographic images arranged from front to back. FIG. 16A shows a stereoscopic left-eye image and FIG. 16B shows a stereoscopic right-eye image. Each of these left-eye and right-eye images is created, for example, as follows.

A stereoscopic left-eye image is created by synthesizing the four transmission images by the maximum intensity projection method.

A stereoscopic right-eye image is created by shifting the vertically-arranged four depth tomographic images, from top to bottom, 8, 6, 4, and 2 pixels in that order to the left of the screen, and synthesizing these by the maximum intensity method.

At each pixel of the stereoscopic image, the maximum intensity of the four depth tomographic images to be synthesized is displayed. In this method, because the speckles in the entire area are equalized, a depth effect cannot be obtained. On the other hand, a high-intensity outline, such as the walls of a blood vessel, is extracted with a depth effect. Therefore, this method can be considered to be useful in acquiring depth information on the passage of a blood vessel in an ultrasound B mode image. With the method, even when a relatively large number of tomographic images are used, a stereoscopic image can be created.

Concerning color images, too, it is possible to use both the method in (A) and the method in (B) by considering the above factors independently for each of the three primary colors, red, green, and blue, used in the present display.

(First Embodiment)

Hereinafter, an ultrasound diagnostic apparatus according to a first embodiment of the present invention will be explained.

Figure 1:
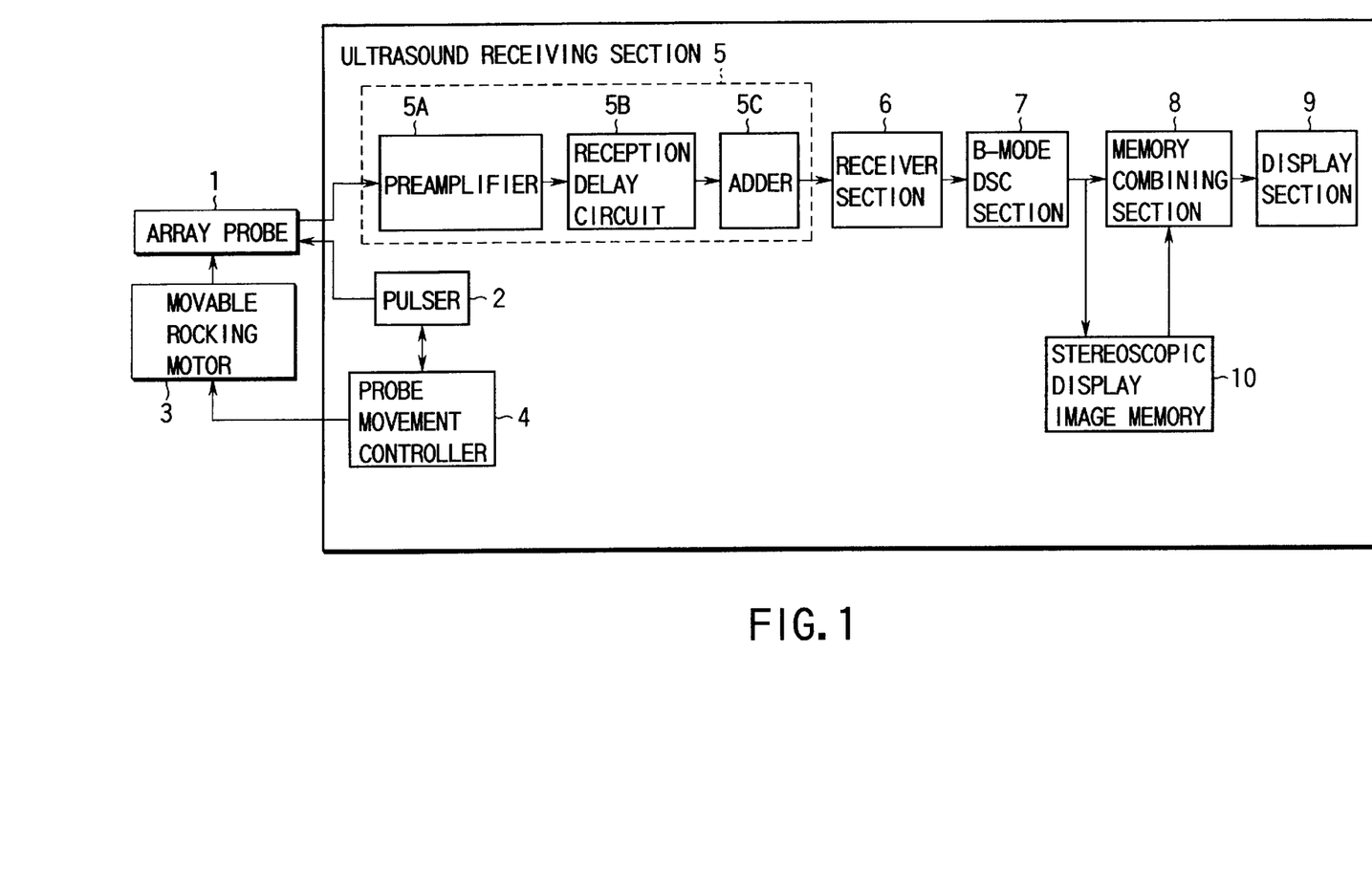
FIG. 1 is a block diagram of the functional configuration of an ultrasound diagnostic apparatus according to a first embodiment of the present invention.

FIG. 1 is a block diagram of the functional configuration of an ultrasound diagnostic apparatus according to the first embodiment of the present invention.

An array probe 1 has a plurality of piezoelectric vibrators acting as electromechanical reversible transducer elements made of, for example, piezoelectric ceramic. These piezoelectric vibrators are arranged in parallel at the tip of the array probe 1. A pulser 2 receives a rate pulse and applies a voltage pulse to the array probe 1 channel by channel according to the timing of the rate pulse. This causes an ultrasonic beam to be transmitted to a subject. A movable rocking motor 3 is provided to mechanically move the array probe 1 in the direction perpendicular to the direction of array. A probe movement controller 4 is provided to synchronize the movable rocking motor 3 with the pulser 2.

The reflected waves from the discontinuous surface of the acoustic impedance in the subject are received by the array probe 1. The echo signal the probe 1 outputs channel by channel is supplied to an ultrasound receiving section 5. The ultrasound receiving section 5 includes a preamplifier 5A, a reception delay circuit 5B, and an adder 5C. The preamplifier 5A amplifies the echo signal channel by channel. The reception delay circuit 5B gives the amplified signal a delay time necessary to determine reception directivity. The adder 5C adds the resulting signals. The addition emphasizes the reflected component in the direction corresponding to the reception directivity. The transmission directivity and reception directivity helps form a comprehensive ultrasonic beam for transmission and reception.

The configuration of a receiver section 6 and subsequent circuits will be explained. The receiver section 6 is composed of a logarithmic amplifier, an envelope detector, and an analog/digital converter (A/D converter), which are not shown here. The output of the receiver section 6 is converted by a B-mode digital scan converter (DSC) section 7 from the ultrasonic scan raster signal train into a video format raster signal train. The converted signal is sent to a memory synthesizing section 8. The memory synthesizing section 8 arranges the images and setting parameters or superposes them to produce a video signal and output the signal. The video signal is sent to a display section 9, on which a tomographic image of the shape of the tissue of the subject is displayed.

When an normal diagnostic image, not a stereoscopic image, is displayed, the signal from the DSC 7 is sent directly to the memory synthesizing section 8. In contrast, when a stereoscopic image related to the present invention is displayed, the signal from the DSC 7 is sent to a stereoscopic display image memory 10. After a stereoscopic image has been created in the memory 10, the resulting image is sent to the memory synthesizing section 8. The stereoscopic display image memory 10 is the principal part of the present invention. The operation of the stereoscopic display image memory 10 will be explained later.

(Method of taking in depth tomographic images)

The following is an explanation of a method of taking in depth tomographic images.

Figure 2A:
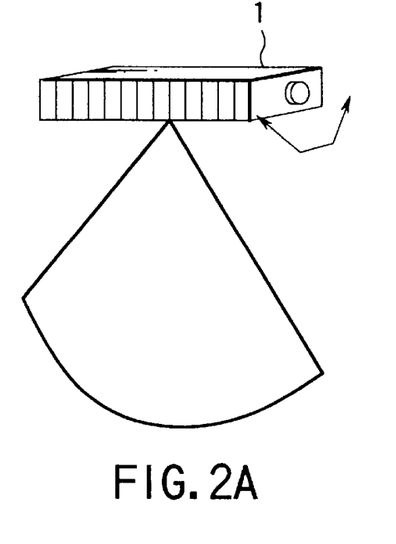
FIG. 2A is a perspective view of the array probe having a rocking mechanism according to the first embodiment.
Figure 2B:
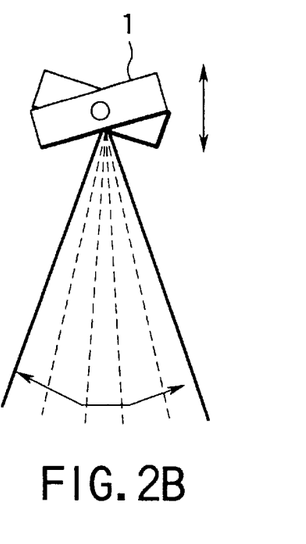
FIG. 2B is a side view of an array probe having a rocking mechanism according to the first embodiment.

With the embodiment, a plurality of tomographic images in the direction perpendicular to the scanning surface are obtained by mechanically moving the array probe 1 provided with the rocking mechanism as shown in FIGS. 2A and 2B. A concrete configuration of the array probe 1 with the rocking mechanism has been disclosed in, for example, Jpn. Pat. Appln. KOKAI No. 55-116342 and Jpn. Pat. Appln. KOKAI No. 61-154653.

Although the embodiment makes use of known examples as mentioned above, it differs from the known examples in the following point. In the above known examples, spatially dense three-dimensional data items are acquired. For example, when there are scanning lines for, for example, 120 rasters in the direction of array, it is necessary to collect as many depth tomographic images as about 120 images in the direction perpendicular to the scanning surface. Accordingly, it takes time to acquire three-dimensional data items.

On the other hand, in the present embodiment, exact three-dimensional information is not needed and two to ten depth tomographic images are obtained in the direction perpendicular to the scanning surface. Therefore, the time required to acquire three-dimensional data items is 100 msec to 300 msec at most.

The following is an explanation of the function of synthesizing a stereoscopic image from the taken-in depth tomographic images and displaying the image.

On the basis of the principle of stereoscopic vision, the stereoscopic display image memory 10 of FIG. 1 does image processing calculations about the depth tomographic images in the direction perpendicular to the array of the probe 1.

Figure 3:
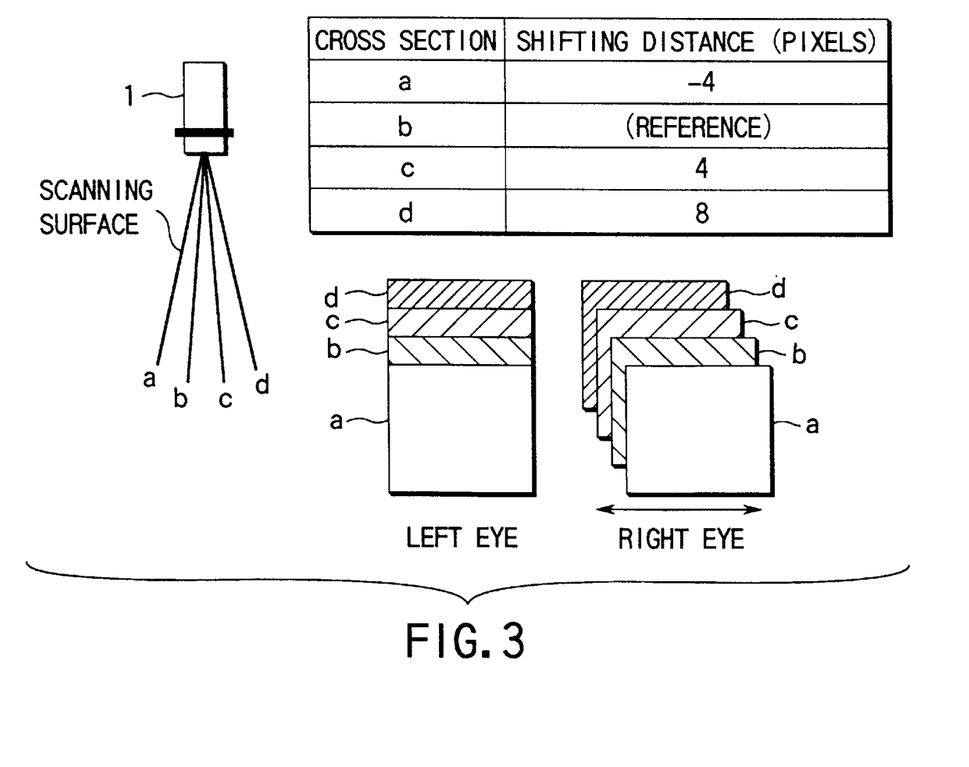
FIG. 3 shows an example of creating a stereoscopic image when scanning is effected at regular intervals in the direction perpendicular to the array of the first embodiment.

FIG. 3 shows the shifting distance of depth tomographic images. A stereoscopic left-eye image is obtained by just making an additive synthesis of the images of cross sections a to d. A stereoscopic right-eye image is obtained by using the image of cross section b among the depth tomographic images composed of cross sections a to d as a reference, shifting the image of cross section a left about four pixels from the reference (or—four pixels right), shifting the image of cross section c right about four pixels from the reference, shifting the image of cross section d right about eight pixels from the reference, and making an additive synthesis of these images of cross sections a to d.

While in the embodiment, the stereoscopic left-eye image is obtained by just making an additive synthesis of the images without shifting the respective images, the images for cross sections for the left eye may be shifted without shifting those for the right eye. Alternatively, the images for cross sections for both the left eye and the right eye may be shifted.

Figure 4:
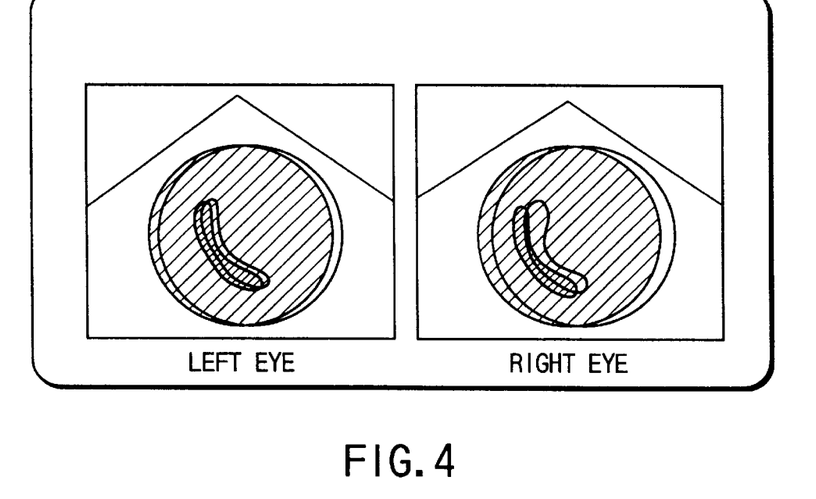
FIG. 4 pictorially shows a display example of a stereoscopic image according to the first embodiment.

In the stereoscopic display memory 10, the image shifting distance (in pixel values) as explained in FIG. 3 has been defined. According to the definition, the images are synthesized. This creates intensity-superposed images as shown in FIGS. 15A and 15B or in FIGS. 16A and 16B (refer to FIG. 4).

In the embodiment, (A) Method of using transmission images and (B) Method of using MIP have been explained. Depending on the number of superposed images (or the number of depth tomographic images), the operator may choose the most suitable method.

A depth effect varies with the shifting distance in creating a stereoscopic image. From a stereoscopic image, the relative back-and-forth relationship can be known. Because the stereoscopic image does not have exact three-dimensional information as described above, it is not suitable for measuring the distance in the direction of depth or the like. Therefore, there is no exact limit on the shifting distance in synthesizing images. (As the shifting distance is made larger, a depth effect is just emphasized more.)

Figure 5:
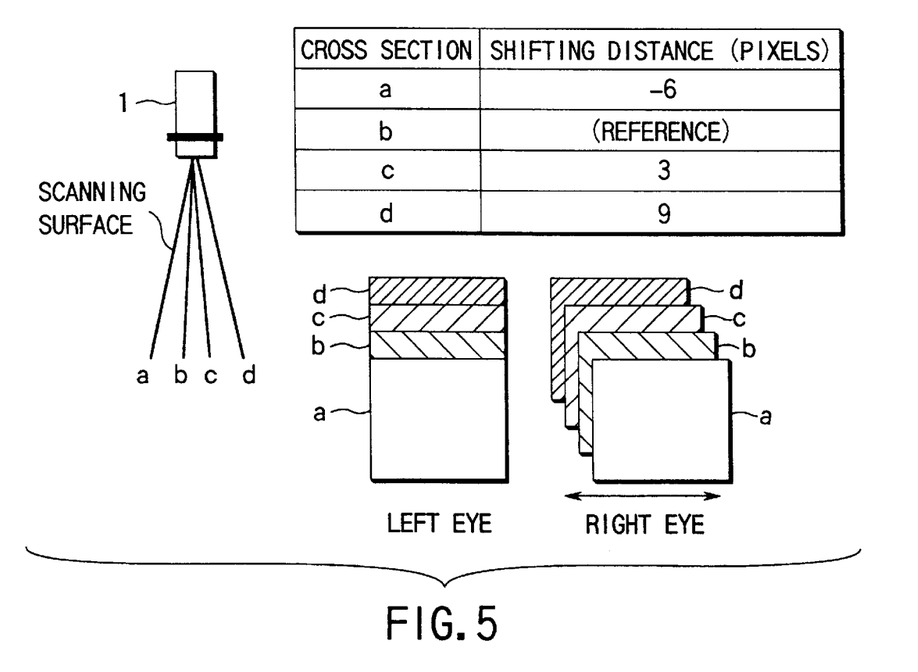
FIG. 5 shows an example of creating a stereoscopic image when scanning is effected at irregular intervals in the direction perpendicular to the array of the first embodiment.

Furthermore, for example, when scanning is effected at irregular intervals as shown in FIG. 5, an irregular depth effect can be realized by varying the shifting distance proportionally.

The problem is that the distance in the direction of depth differs with depth, because the actual tomographic planes produced by the array probe 1 are not parallel with each other as seen from FIGS. 3 and 5. When the present invention is used only to give a depth effect, the methods shown in FIGS. 3 and 5 produce a sufficient effect. Moreover, it is easy to know the back-and-forth relationship or the relative positional relationship, such as the relationship between a blood vessel crossing the scanning surface and a blood vessel running in the direction perpendicular to the scanning surface.

Figure 6:
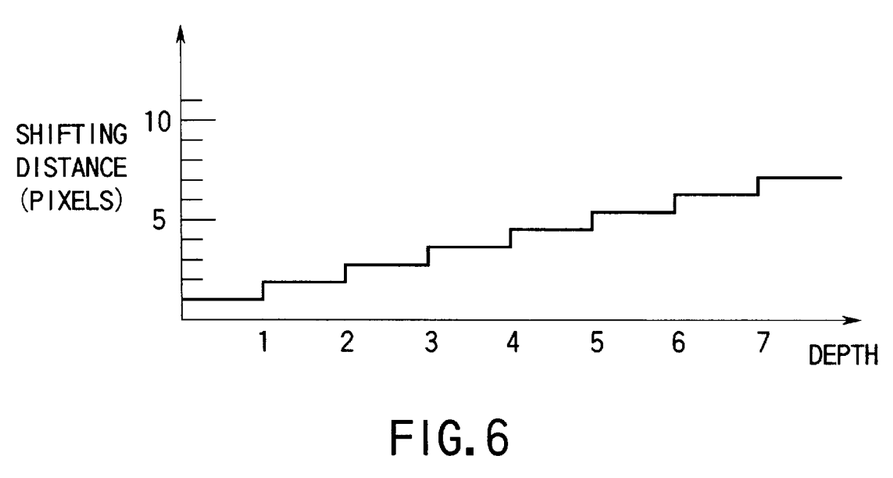
FIG. 6 shows an example of correcting the shifting distance in the first embodiment.

To correct the variation of the distance in the direction of depth with depth, the shifting distance is changed according to the depth of a tomographic image as shown in FIG. 6. In the example of FIG. 6, images are defined in such a manner that portions whose depth ranges from 0 to 1 cm are shifted one pixel and portions whose depth ranges from 1 to 2 cm are shifted two pixels.

The stereoscopic display image memory 10 synthesizes the received images one after another as described above and supplies the resulting images to the display section 9 via the memory synthesizing section 8. Therefore, when a stereoscopic image is created using, for example, three to four images, the frame rate of the diagnostic images is decreased to ¼ to ⅓ of the original rate at most and an image with a depth effect can be displayed in real time.

Furthermore, the method enables a stereoscopic image to be displayed on the monitor of a conventional diagnostic apparatus without using a special display. Of course, a special display for displaying a stereoscopic image may be used. This will be explained in a second embodiment of the present invention explained below.

(Second Embodiment)

Figure 7:
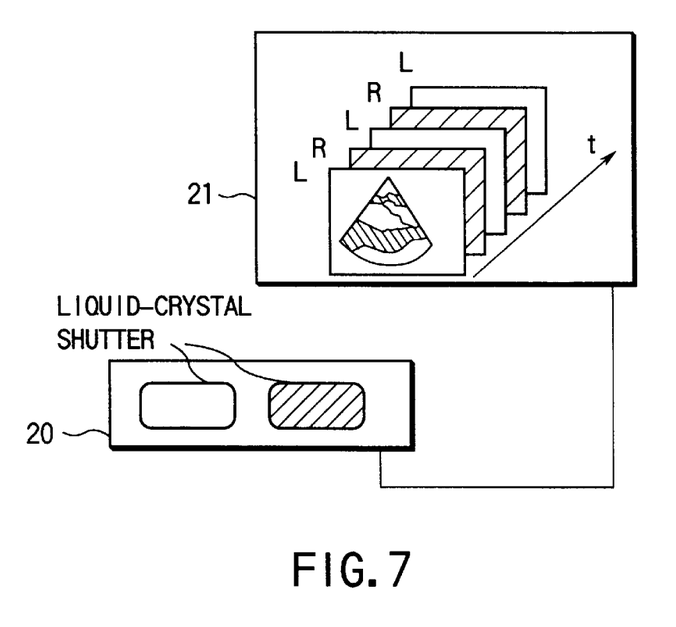
FIG. 7 is an explanatory diagram of a time-division stereoscopic television system making use of a liquid-crystal shutter glasses according to a second embodiment of the present invention.

Stereoscopic vision with the naked eye requires experience. Some people need more experience and others need less experience before they have stereoscopic vision. In most ordinary examinations, the display and the subject are viewed alternately. This may makes stereoscopic vision with the naked eye difficult. To solve this problem, in the second embodiment, a time-division stereoscopic television system using liquid-crystal shutter glasses 20 often used in the X-ray diagnostic apparatus is applied to a display 21 of an ultrasound diagnostic apparatus as shown in FIG. 7. In the system, a right image and a left image are presented alternately in the field period t of the display 21 and the liquid-crystal shutter glasses 20 are opened and closed in synchronism with the alternation to provide stereoscopic vision.

Furthermore, wearing special glasses for stereoscopic vision may be a lot of trouble. To avoid this trouble, a parallax stereogram may be applied to the display system in place of the time-division stereoscopic television system using the liquid-crystal shutter glasses. The display method using a parallax stereogram has recently been used as a stereoscopic color liquid-crystal display. It is a method of allowing the viewer to see a right image and a left image separately through slit-like openings.

Although the second embodiment uses a special display system, it produces the effect of alleviating a burden on the operator observing a stereoscopic image. Since the number of depth tomographic images needed for stereoscopic vision as described in the first embodiment is smaller than when dense three-dimensional images are constructed, a load on the display system is light and therefore the real-time display feature is not impaired.

(Third Embodiment)

As a third embodiment of the present invention, an ultrasound diagnostic apparatus which uses a two-dimensional (2D) array probe for getting tomographic images and effects color Doppler imaging will be explained.

Figure 8:
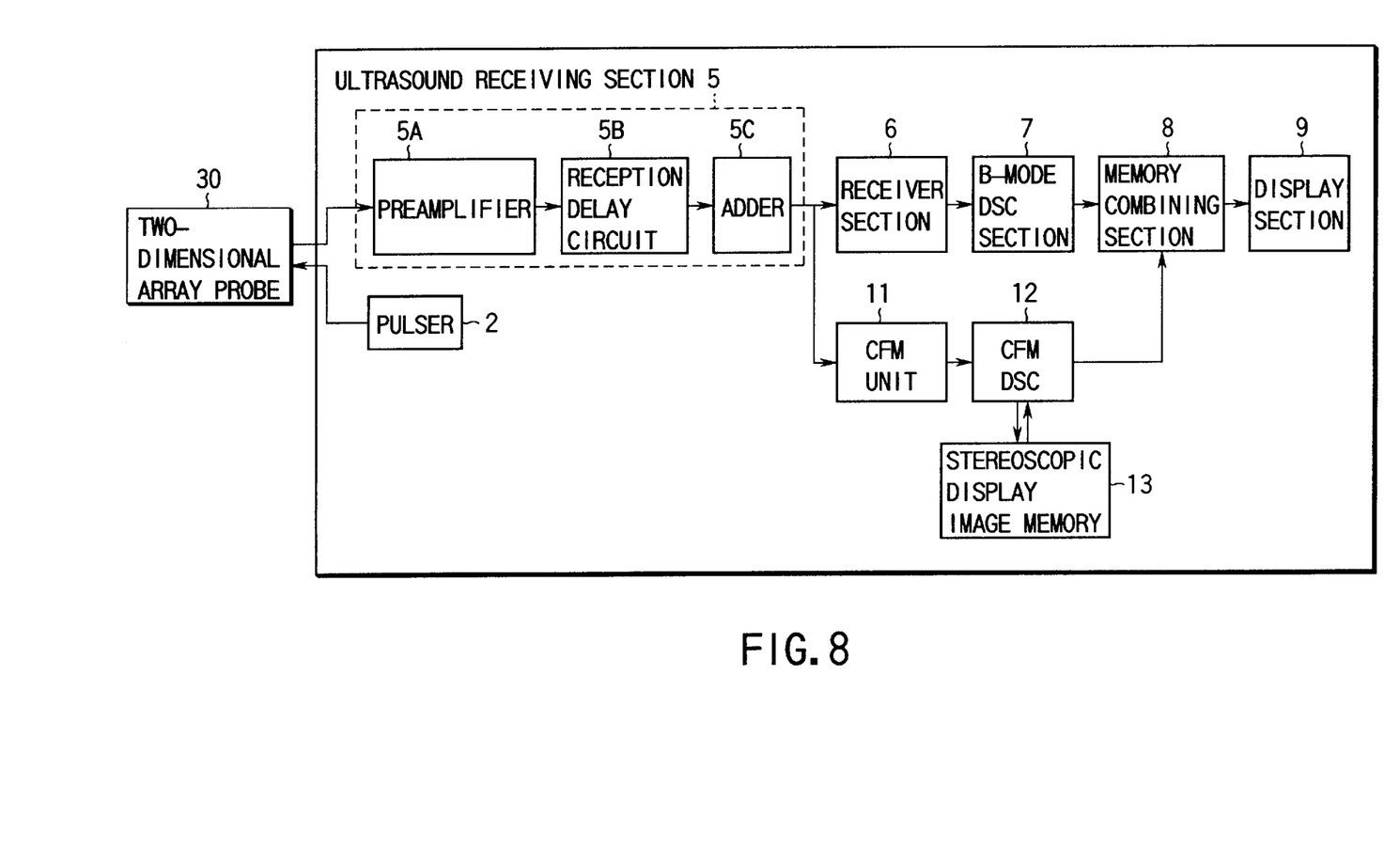
FIG. 8 is a block diagram of the functional configuration of an ultrasound diagnostic apparatus according to a third embodiment of the present invention.

FIG. 8 is a block diagram of the functional configuration of an ultrasound diagnostic apparatus according to the third embodiment of the present invention.

One known method is to use a two-dimensional array probe 30 and effect three-dimensional scanning in the direction of array and the direction of slice. By using this method in place of the array probe 1 provided with the rocking mechanism in the first embodiment, a plurality of tomographic images can be obtained rapidly. The third embodiment is the application of the present invention to color Doppler imaging. The configuration of an apparatus including a CFM process relating to color Doppler imaging will be explained.

A signal for generating a color Doppler image is sent to a CFM unit 11. The CFM unit 11 is composed of a detector, a clutter removing filter, and a Doppler shifted wave count analyzer, which are not shown here. The CFM unit 11 produces the speed V of, the power P of, or the dispersion σ of a moving object (e.g., bloodstream). The output signal from the CFM unit 11 is supplied to a CFM digital scan converter (DSC) 12 and then to the memory synthesizing section 8.

In the third embodiment, there is provided a stereoscopic display image memory 13 for CFM. The memory 13 may overlap with the B-mode stereoscopic display image memory, as long as it is capable of synthesizing color images. When independent single colors are considered to be basic colors, for example, red, green, and blue, in color images, the method of using transmission images, the method of using MIP, and the method using gray scale can be applied to color images.

As described above, with the first to third embodiments, use of a relatively small number of images enables a simple ultrasonic three-dimensional image with a depth effect to be displayed at high speed. This enables the operator to quickly know the passage of a blood vessel in the direction of depth perpendicular to a tomographic image and the relative positional relationship, including the relationship between a blood vessel crossing the scanning surface and a blood vessel running in the direction perpendicular to the scanning surface.

(Fourth Embodiment)

The ultrasound diagnostic apparatus in each of the first to third embodiments is an apparatus for collecting ultrasonic images related to different cross sections of the subject, creating an ultrasonic three-dimensional image with a depth effect on the basis of the collected images, and displaying the stereoscopic image. A fourth embodiment of the present invention relates to an apparatus for collecting ultrasonic images of the same cross section of the subject at different times in flash echo imaging, creating a stereoscopic image from the collected images by the same method in each of the first to third embodiments, and displaying the stereoscopic image.

The most basic diagnosis by the contrast echo method using a contrast agent is a diagnosis in which the presence or absence of a bloodstream in the diagnosed part is known by checking for the presence or absence of the increase of intensity using a contrast agent. A more advanced diagnosis is a diagnosis in which the change of the spatial distribution of a contrast agent in the diagnosed part with respect to time is observed on the basis of the spread of changes in the intensity or the degree of an increase in the intensity. Another advanced diagnosis is a diagnosis in which the time from when a contrast agent is injected until it reaches the region of interest (ROI), the change of echo intensity with time (TIC: Time Intensity Curve) caused by the contrast agent in the ROI, or the maximum intensity are observed.

Such a contrast echo method using a contrast agent is more effective in use with a harmonic imaging method. The harmonic imaging method is a method of separating the higher harmonic components created by nonlinear behaviors caused by ultrasonically excited very small air bubbles from the basic frequency component and visualizing them. Since the internal organs is relatively less liable to behave in a nonlinear manner, the contrast agent can be observed with a good contrast ratio.

Known ones of the imaging methods positively making use of the phenomenon disappearing by the projection of ultrasound are "flash echo imaging (reference: Naohisa Kamiyama, et al., "Evaluation of the 6795 flash echo imaging method (1)," the $67^{th}$ Japanese Ultrasonic Medical Society Meeting, June, 1996)", and "Trangient Response Imaging."

The principle of the flash echo imaging method is as follows.

The time required for very small air bubbles to flow into the region of interest and crowd together is given by switching the continues scanning at a rate of several tens of frames per second in the prior art to intermittent scanning at a rate of one frame in several seconds. As soon as very small air bubbles have crowded together in the region of interest, transmission and reception are carried out using ultrasound with high sound pressure, thereby producing a high contrast echo signal. With such a flash echo imaging method, the increase of intensity is improved.

With the ultrasound diagnostic apparatus in each of the first to third embodiments, a plurality of ultrasonic images related to different cross sections of the subject are collected and an ultrasonic three-dimensional image with a depth effect is created on the basis of the collected images. On the other hand, with the ultrasound diagnostic apparatus according to the fourth embodiment, the flash echo imaging is effected, collecting ultrasonic images of the same cross section of the subject at different times in the flash echo imaging, creating a stereoscopic image from the collected images, and displaying the stereoscopic image.

Figure 17:
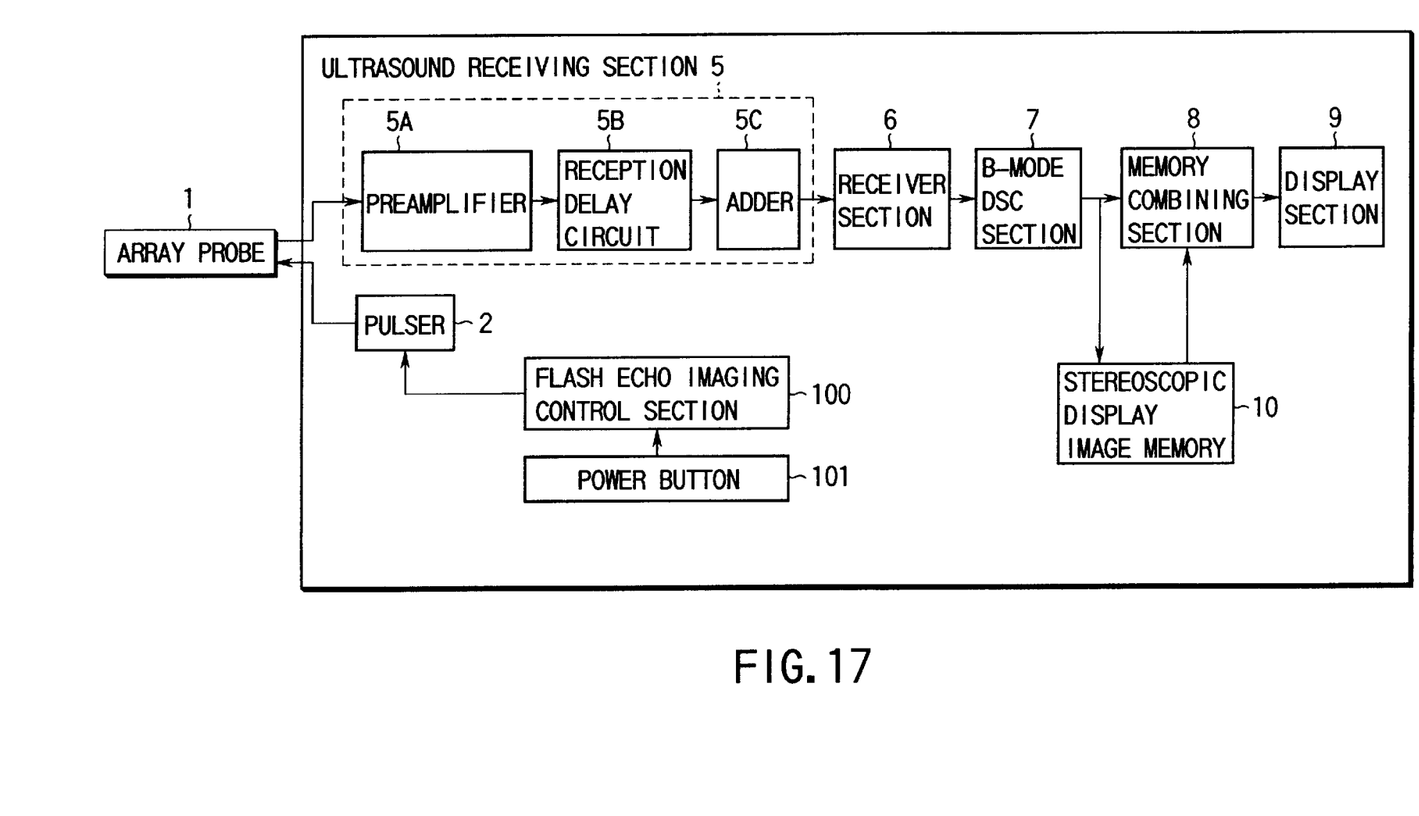
FIG. 17 is a schematic block diagram of an ultrasound diagnostic apparatus according to a fourth embodiment of the present invention.

FIG. 17 is a schematic block diagram of the ultrasound diagnostic apparatus according to the fourth embodiment of the present invention.

With the ultrasound diagnostic apparatus of the fourth embodiment, because ultrasonic images of the same cross section, not of different ones, of the subject are collected and used to create a stereoscopic image, there is no need for a mechanism for causing the movable rocking motor 3 to mechanically move the array probe 1 in the direction perpendicular to the direction of array as explained in the first embodiment. Moreover, the ultrasound diagnostic apparatus of the fourth embodiment is provided with a flash echo imaging control section 100 and a power button 101, which act as means for effecting flash echo imaging. The flash echo imaging in the fourth embodiment is designed for the operator (not shown) to perform a manual operation. When the operator operates the power button 101, this changes the sound pressure. In response to the operation of the power button 101, the flash echo imaging control section 100 controls the pulser 2 for driving the array probe 1, which causes the sound pressure to be switched.

The remaining configuration of FIG. 1 is the same as that of the first embodiment.

When flash echo imaging is effected with the ultrasound diagnostic apparatus of the fourth embodiment, the echo signal for one frame in the first scan in which the sound pressure has been changed from a relatively low one to a relatively high one is obtained with a high sensitivity proportional to the high sound pressure. This produces a B-mode image, where a contrast-agent-existing part R1 has been extracted clearly with high intensity. It is natural to think that in the B-mode image, all the parts without the contrast agent also have high intensity. Most of the very small air bubbles that have been hit by ultrasound with relatively high sound pressure disappear. Consequently, after the sound pressure has changed relatively greatly, the intensity of the part R2 where the contrast agent was present decreases in the B-mode images obtained by two scans or several scans. Of course, the intensity of the parts without the contrast agent remains unchanged.

As described above, although momentarily, a frame where the echo intensity of the contrast-agent-existing part is very high is obtained and a series of frames where the echo intensity of the contrast-agent-existing parts is low after very small air bubbles have collapsed is obtained. The number of consecutive frames whose echo intensity is low is assumed to be, for example, three. It goes without saying that the number of frames is not limited to three. The number of frames whose echo intensity is very high is also not limited to one.

Figure 18A:
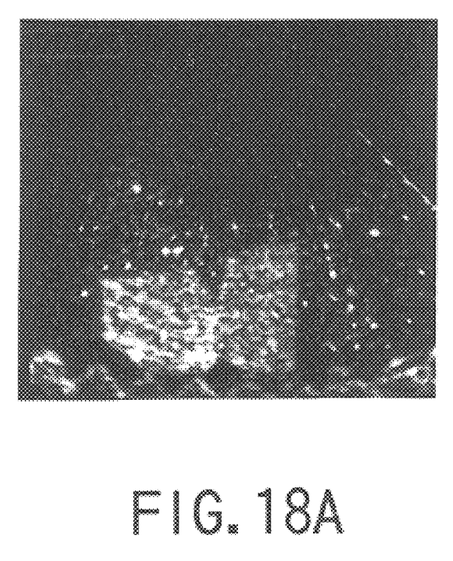
FIG. 18A is a color photograph showing a display example of an image for the left eye by an flash echo imaging method.
Figure 18B:
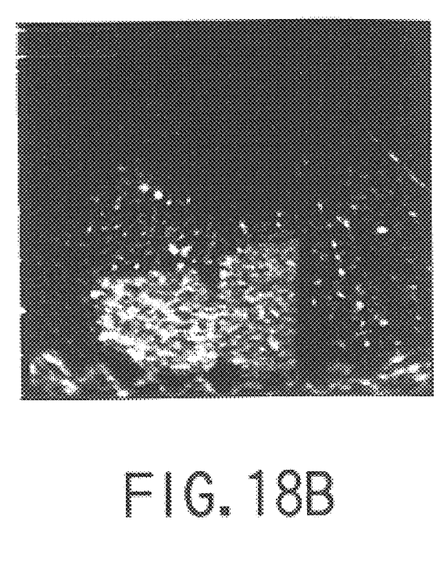
FIG. 18B is a color photograph showing a display example of an image for the right eye by an flash echo imaging method.

The frames of cross sections a, b, c, and d in the first embodiment are replaced with the frames in the fourth embodiment. Specifically, the frame of cross section a is replaced with the frame whose echo intensity is very high. The frames of cross sections b, c, and d are replaced with the series of frames (three frames) whose echo intensity is low. As in the method explained in the first embodiment, a right-eye image (shown by FIG. 18B in this embodiment) and a left-eye image (shown by FIG. 18A in this embodiment) can be obtained by shifting each of those frames differently and making an additive synthesis of them.

The contents written in the first and second embodiments are applied easily to the way of creating a right-eye image and a left-eye image and the display method in the fourth embodiment.

As described above, with the ultrasound diagnostic apparatus of the fourth embodiment, flash echo imaging is effected, ultrasonic images of the same cross section of the subject are collected at different times in the imaging, a stereoscopic image is created from the collected images, and the stereoscopic image is displayed.

In a stereoscopic image of the fourth embodiment, the contrast-agent-existing part extracted into a frame is observed as if it were in relief. The frame has been obtained by increasing the sound pressure at the time when very small air bubbles have crowded together in the region of interest. This provides a different diagnostic function from when images of many frames obtained from flash echo imaging are just arranged on the display screen for comparison. Moreover, it is easy to identify a part dyed with a contrast agent.

The present invention is not limited to the above-described embodiments and may be practiced or embodied in still other ways without departing from the spirit or essential character thereof.

As described above, with the present invention, it is possible to provide an ultrasound diagnostic apparatus capable of displaying ultrasound diagnostic images with a depth effect at high speed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

I claim:

1. An ultrasound diagnostic apparatus comprising:
    image collecting means for collecting a plurality of ultrasonic images in a direction perpendicular to a tomographic plane;
    right-eye image synthesizing means for obtaining a right-eye image by synthesizing said plurality of ultrasonic images collected by said image collecting means such that the ultrasonic images are shifted from each other in a direction parallel to the tomographic plane by a first way of shifting;
    left-eye image synthesizing means for obtaining a left-eye image by synthesizing said plurality of ultrasonic images collected by said image colleting means such that the ultrasonic images are shifted from each other in a direction parallel to the tomographic plane by a second way of shifting, which is different from the first way of shifting, the difference between the first and second ways of shifting being based on a parallax of both eyes; and
    display means for displaying said right-eye image and said left-eye image separately.

2. An ultrasound diagnostic apparatus according to claim 1, wherein said image collecting means comprises a two-dimensional array ultrasonic probe in which ultrasonic oscillators are arranged two-dimensionally, and
    said image collecting means collects said ultrasonic images on the basis of the echo signal from said two-dimensional array ultrasonic probe.

3. An ultrasound diagnostic apparatus according to claim 1, wherein said image collecting means includes an ultrasonic probe including ultrasonic vibrators arranged one-dimensionally and means for mechanically rocking the ultrasonic vibrators in a direction perpendicular to the direction in which the ultrasonic vibrators are arranged.

4. An ultrasound diagnostic apparatus according to claim 1, wherein said display means displays said right-eye image and said left-eye image side by side.

5. An ultrasound diagnostic apparatus according to claim 1, wherein said display means displays said right-eye image and said left-eye image in a time-division manner.

6. An ultrasound diagnostic apparatus according to claim 1, wherein said ultrasonic images are composed of B-mode images and color Doppler images superposed on the B-mode images.

7. An ultrasound diagnostic apparatus comprising:
    image collecting means for collecting an ultrasonic image where an echo intensity of a contrast-agent-existing part is high and further collecting a series of ultrasonic images at times different from the time at which the above image was collected, the echo intensity of said contrast-agent-existing part is high and further collecting a series of ultrasonic images at times different from the time at which the above image was collected, the echo intensity of said contrast-agent-existing part in each of the images being low;

right-eye image synthesizing means for obtaining a right-eye image by synthesizing said plurality of ultrasonic images collected by said image collecting means such that the ultrasonic images are shifted from each other in a direction parallel to the tomographic plane by a first way of shifting;

left-eye image synthesizing means for obtaining a left-eye image by synthesizing said plurality of ultrasonic images collected by said images collecting means such the ultrasonic images are shifted from each other in a direction parallel to the tomographic plane by a second way of shifting, which is different from the first way of shifting, the difference being the first and second ways of shifting being based on a parallax of both eyes; and display means for displaying said right-eye image and said left-eye image separately.

8. An ultrasound diagnostic apparatus according to claim 7, wherein said display means displays said right-eye image and said left-eye image side by side.

9. An ultrasound diagnostic apparatus according to claim 7, wherein said display means displays said right-eye image and said left-eye image in a time-division manner.

10. An ultrasound diagnostic apparatus according to claim 1, wherein said right-eye image synthesizing means obtains said right-eye image by synthesizing the shifted ultrasonic images in accordance with an MIP method, and said left-eye synthesizing means obtains said left-eye image by synthesizing the shifted ultrasonic images in accordance with the MIP method.

11. An ultrasound diagnostic apparatus according to claim 1, wherein said right-eye image synthesizing means obtains the right-eye image by adding the shifted ultrasonic images on each other so that a transmission image is obtained, and the left-eye image by adding the shifted ultrasonic images on each other so that a transmission image is obtained.

12. An ultrasound diagnostic apparatus according to claim 1, wherein said display means displays a right-eye image obtained by said right-eye image synthesizing means and a left-eye image obtained by said left-eye image synthesizing means on one screen.

* * * * *